(12) United States Patent
Grahn et al.

(10) Patent No.: US 7,122,047 B2
(45) Date of Patent: Oct. 17, 2006

(54) CONTROLLED HEAT TRANSFER WITH MAMMALIAN BODIES

(75) Inventors: Dennis A. Grahn, Palo Alto, CA (US); H. Craig Heller, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/714,488

(22) Filed: Nov. 14, 2003

(65) Prior Publication Data

US 2005/0103353 A1 May 19, 2005

(51) Int. Cl.
*A61F 7/00* (2006.01)

(52) U.S. Cl. ............... 607/108; 128/898; 607/112; 607/96

(58) Field of Classification Search .......... 607/96, 607/104, 108, 112; 128/898
See application file for complete search history.

(56) References Cited

U.S. PATENT DOCUMENTS

| | | | |
|---|---|---|---|
| 4,149,529 A | 4/1979 | Copeland et al. | |
| 4,376,437 A | 3/1983 | Sundheim et al. | |
| 5,074,285 A | 12/1991 | Wright | |
| 5,358,467 A | 10/1994 | Milstein et al. | |
| 5,683,438 A | 11/1997 | Grahn | |
| 5,688,225 A | 11/1997 | Walker | |
| 6,149,674 A | 11/2000 | Borders | |
| 6,258,046 B1* | 7/2001 | Kimball et al. | 600/593 |
| 6,508,831 B1 | 1/2003 | Kushnir | |
| 6,572,638 B1* | 6/2003 | Dae et al. | 607/96 |
| 6,685,731 B1* | 2/2004 | Kushnir et al. | 607/104 |
| 6,719,780 B1* | 4/2004 | Salmon et al. | 607/108 |
| 2003/0040783 A1* | 2/2003 | Salmon | 607/111 |
| 2003/0236487 A1* | 12/2003 | Knowlton | 604/20 |

FOREIGN PATENT DOCUMENTS

WO WO 98/40039 9/1998

OTHER PUBLICATIONS

Bergersen et al., "Perfusion of the human finger during cold-induced vasodilation" *American Physiological Society* R731-R737 (1999).
Bergersen et al., "Local contriction of arteriovenous anastomosis in the cooled finger" *American Physiological Society* R880-R886 (1997).
Bergersen et al., "Effect of local warming on hand and finger artery blood velocities" *American Physiological Society* R325-R330 (1995).

(Continued)

*Primary Examiner*—Roy D. Gibson
(74) *Attorney, Agent, or Firm*—Bret E. Field; Bozicevic, Field & Francis, LLP

(57) ABSTRACT

Methods, computer programming and devices for transferring heat to and/or from a body portion of a mammal are provided. One approach includes directly determining a state of vasoconstriction or vasodilation in a portion of a body, and supplying heat to the portion of the body when vasoconstriction is determined, and removing heat from the portion of the body when vasodilation is determined. The body portion preferably includes specific heat exchange vasculature. In another approach, a transition of the body portion from a state of vasodilation to vasoconstriction is determined and the body portion is then actively kept in a state of vasodilation while removing heat therefrom.

44 Claims, 14 Drawing Sheets

OTHER PUBLICATIONS

Booth et al., "Improved running performance in hot human conditions following whole body precooling," *Med. Sci. Sports Exerc.*, 29(7):943-9 (Jul. 1997).

Brown et al., "The Effect of Head Cooling on Deep Body Temperature and Thermal Comfort in Man" *Aviat. Space Environ. Med.*, 53:583-586 (1982).

Bruck et al., "Body Temperature Related Factors Diminishing the Drive to Exercise," *Can J. Physiol. Pharmacol.*, 65(6):1274-80 (Jun. 1987).

Capello et al., "Lowering Body Temperature with a Cooling Suit as Symptomatic Treatment for Thermosensitive Multiple Sclerosis Patients," *Ital. J. Neurol. Sci.*, 16:533-539 (1995).

Gonzalez-Alonso et al., "Influence of Body Temperature on the Development of Fatigue During Prolonged Exercise in the Heat," *J. Appl. Physiol.*, 86(3):1032-9 (Mar. 1999).

Gordon et al., "Effect of a Practical Neck Cooling Device on Core Temperature During Exercise" *Med. Sci. Sports Exerc.*, 22:245-249 (1998).

Grahn et al. "Recovery from mild hypothermia can be accelerated by mechanically distending blood vessels in the hand" *The American Physiological Society*, 85(5):1643-1648 (1998).

Greenhaff et al., "Predictors of Sweat Loss in Man During Prolonged Exercise," *Eur. J. Appl. Physiol.*, 58(4):348-52 (1989).

Hessemer et al., "Effect of Slightly Lowered Body Temperatures on Endurance Performance in Humans" *J. Appl. Physiol.*, 57(6):1731-7 (Dec. 1984).

Katsuura et al., "Effects of Cooling Portions of the Head on Human Thermoregulatory Response," *Appl. Human Sci.*, 15:67-74 (1996).

Ku et al., "Physiological and Thermal Responses of Male and Female Patients with Multiple Sclerosis to Head and Neck Cooling," *Am. J. Phys. Med. Rehabil.*, 78:447-456 (Sep.-Oct. 1999).

Ku et al., "Hemodynamic and Thermal Responses to Head and Neck Cooling in Men and Women," *Am. J. Phys. Med. Rehabil.*, 75:443-450 (Nov.-Dec. 1996).

Lee et al., "Exercise Duration and Thermoregulatory Responses After Whole Body Precooling," *J. Appl. Physiol.*, 79(6):1971-6 (Dec. 1995).

Leweke et al., "Temperature Effects on Ventilatory Rate, Heart Rate, and Preferred Pedal Rate During Cycle Ergometry," *J. Appl. Physiol.*, 79(3):781-5 (Sep. 1995).

Marsh et al., "Effect on Precooling on High Intensity Cycling Performance," *Br. J. Sports Med.*,, 33(6):393-7 (Sep. 1999).

Olschewski et al., "Thermoregulatory, Cardiovascular, and Muscular Factors Related to Exercise After Precooling," *J. Appl. Physiol*, 64(2):803-11 (Feb. 1988).

Schmidt et al., "Effect of a precooling maneuver on body temperature and exercise performance," *J. Appl. Physiol.* 50(4):772-8 (Apr. 1981).

Soreide et al. "A Non-invasive means to effectively restore normothermia in cold stressed individuals: A Preliminary Report" *The Journal of Emergency Medicine*, 17(4)725-730 (1999).

Watanuki, "Effects of Head Cooling on Cardiovascular and Body Temperature Responses During Submaximal Exercise." *Ann. Physiol. Antrhopol.* 12:327-333 (1993).

\* cited by examiner

System Architecture

**FOOT INTERFACE
& RELATED SENSORS**

HEAD, SHOULDERS, CHEST, BACK, TORSO AND ARMS

THE ENTIRE SKIN SURFACE

HEAD, SHOULDERS, CHEST AND BACK

HEAD, SHOULDERS, CHEST, BACK AND ARMS

SHOULDERS, CHEST, BACK AND TORSO

SHOULDERS, CHEST, BACK AND ARMS

TORSO AND LEGS

CHEST, BACK, TORSO AND LEGS $T_{Interface}$ affects Vasoconstriction & Vasodilation
(as measured by Blood Flow)

For each individual,
- Vasoconstriction [VC] occurs   below a certain Temp range
- Vasoconstriction [VD] occurs   above that Temp range Blood Flow can be measured by:
- Laser Doppler
- Bio-Impedance
- Light Absorbtion (Pulse Oximetry)

Hysterysis:

The transition between Vasoconstriction and Vasodilation is

NOT Identically Reversible...

The transition occurs at a different temperature range depending on the initial condition Typically, the transition from:
$$VC \longrightarrow VD$$
occurs at a $T_{Interface}$ range above
$$VD \longrightarrow VC$$

If Vasodilation is initially detected

Ⓐ Blood Flow Sensor detects VD, $T_{Interface} = T_{set}$

Ⓑ System controller decreases $T_{Interface}$ until VC detected

Ⓒ $T_{Interface}$ increases above transition temp range, VD occurs

Ⓓ System controller decreases $T_{Interface}$ to $T_{Max\ Heat\ Transfer}$ $T_{Max\ Heat\ Transfer} < T_{set}$ If Vasoconstriction is initially detected (A) Blood Flow Sensor detects VC, $T_{Interface} = T_{set}$ (B) System controller increases $T_{Interface}$ (C) $T_{Interface}$ increases above transition temp range, VD occurs (D) System controller decreases $T_{Interface}$ to $T_{Max\ Heat\ Transfer}$ $T_{Max\ Heat\ Transfer} > T_{set}$

CONTROLLED HEAT TRANSFER WITH MAMMALIAN BODIES

FIELD OF THE INVENTION

The field of this invention relates generally to thermoregulatory status of mammals, and more particularly to the control and management of heat transfer with mammalian bodies.

BACKGROUND

Mammalian body temperature is normally controlled by an internal autonomic regulatory system referred to herein as the thermoregulatory system. One important effector in this system is by controlled by blood flow to specialized skin areas of the body at non-hairy skin surfaces (i.e., at the palms, soles of the feet, cheeks/nose regions). Subcutaneous to these areas, there are unique anatomical vascular structures called venous plexuses. These structures serve to deliver large volumes of blood adjacent the skin surface. By this delivery of blood, significant heat transfer is enabled for the maintenance of internal organs within a functional temperature range. Blood is permitted to pass through the venous plexuses "radiator" structures by way of arterio venous anastamosis, or AVAs that gate or control the arterial input side of the venous plexuses. Thus, the AVA's serve an integral part of the heat transfer system, providing thermoregulatory control. Together, the AVA's and venous plexuses comprise a body's relevant heat exchange vasculature.

Normally, when body and/or environmental temperatures are high, dilation of certain blood vessels favors high blood flow to the noted heat exchange surfaces, thus increasing heat loss to the environment and reduction in the deep body core region temperature. As environmental and/or body temperatures fall, vasoconstriction reduces blood flow to these surfaces and minimizes heat loss to the environment.

There are situations, however, in which it would be desirable to manipulate the transfer of heat across skin surfaces to lower and/or raise the core body temperature. Such core body cooling or heating would be useful in a number of applications, including therapeutic treatment regimens and as a component of improving athletic or industrial performance.

The present invention is geared to improvement implementation of these goals. It does so in various ways by specifically taking natural vasoconstriction tendencies into account in order that unintended vasoconstriction (during an intended procedure) will not adversely effect blood flow in the region of a heat transfer surface so as to prevent adequate heat transfer.

SUMMARY OF THE INVENTION

Methods and devices for manipulating and controlling the thermoregulatory status of a mammal are provided. Software or programming for effecting such methodology and running the subject hardware also forms part of the subject invention.

In one aspect of the invention, a method includes transferring heat to and/or from a body portion of a mammal. The method includes determining a state of vasoconstriction or vasodilation in a portion of a body, and supplying heat to the portion of the body when and where vasoconstriction is determined, and removing heat from the portion of the body when and where vasodilation is determined. The act of determining vasoconstriction or vasodilation includes sensing a characteristic of the body associated with the state of vasoconstriction or vasodilation, (e.g., blood flow rate to the body portion) at the site of interest, (i.e., where heat transfer it to be effected).

In another aspect of the invention, a transition of the body portion from a state of vasodilation to or from vasoconstriction is prompted and the body portion is then kept in a state of vasodilation while removing heat therefrom. An exemplary method includes inducing a transition of the body portion from a state of vasodilation to vasoconstriction by removing heat from the body portion. A determination of a transition temperature associated with the transition from vasodilation to vasoconstriction is then made. Next, the method reestablishes vasodilation in the body portion and removes heat from the body portion at a temperature equal to or greater than the transition temperature. In another example, if the body portion is initially in vasoconstriction, heat is supplied until vasodilation occurs in the body portion prior to inducing the transition from vasodilation to vasoconstriction.

The present invention is better understood upon consideration of the detailed description below in conjunction with the accompanying drawings and claims.

BRIEF DESCRIPTION OF THE FIGURES

Each of the figures diagrammatically illustrates aspects of the invention. Of these figures.

DETAILED DESCRIPTION

Figure 1:
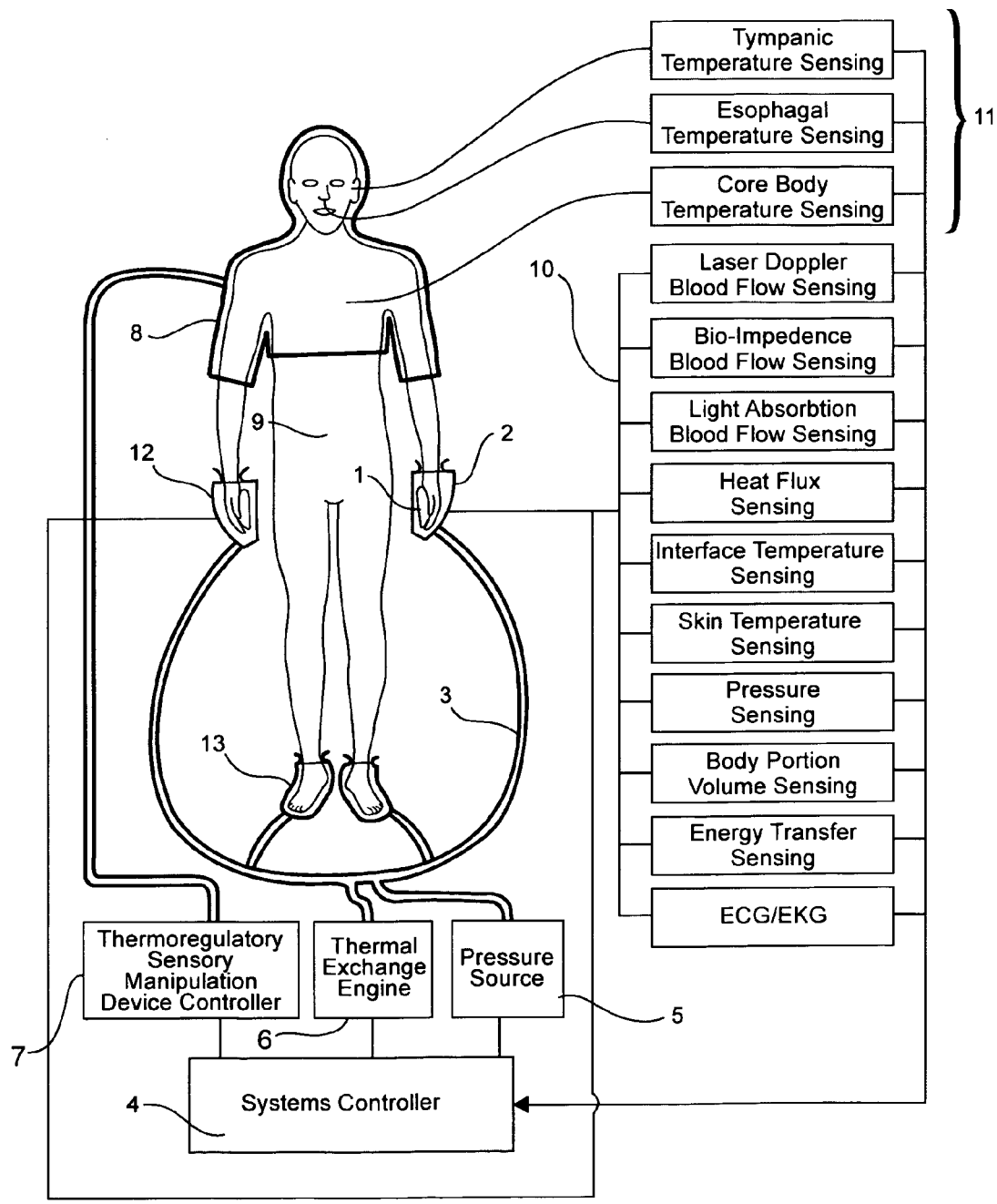
FIG. 1 illustrates exemplary system architecture for controlled heat transfer with mammalian bodies.

Before the present invention is described in detail, it is to be understood that this invention is not limited to particular variations set forth and may, of course, vary. Methods and devices for manipulating the thermoregulatory status of a mammal are provided. The following description is presented to enable any person of ordinary skill in the art to make and use the inventions. Descriptions of specific techniques and applications are provided only as examples. Various modifications to the examples described herein will be readily apparent to those skilled in the art, and the general principles defined herein may be applied to other examples and applications without departing from the spirit and scope of the invention. Thus, the present invention is not intended to be limited to the examples described and shown, but is to be accorded the widest scope consistent with the principles and features disclosed herein.

Methods recited herein may be carried out in any order of the recited events which is logically possible, as well as the recited order of events—explicit or implied. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

Methodology

Heat transfer from the skin areas of a mammalian body that include heat exchange vasculature, to the outside environment generally occurs when the environmental temperature in the area of these body portions is less than the temperature of the skin. This temperature difference creates a temperature gradient which drives heat energy from the circulating blood of the mammalian body to the outside environment, thereby cooling the core body of the mammal through the circulating blood. However, if the temperature gradient across the skin surface of these body portions is too great, the body's natural thermoregulatory system causes the blood vessels in these areas to constrict, resulting in a reduction in blood flow and blood circulation to these areas. The reduction in blood flow and blood circulation reduces heat transfer from the core body to the outside environment via the body portions including AVAs.

As the environmental temperature in contact with the body portions containing heat exchange vasculature is gradually decreased, but above a temperature where vasoconstriction occurs, heat transfer away from the body increases until the vasoconstriction temperature is reached, at which point the blood vessels constrict, reducing blood flow to the body portion. Generally, heat transfer away from the body decreases significantly and suddenly as the temperature falls and triggers vasoconstriction, for example, resulting in a step shaped function if one were to plot heat transfer or blood flows against temperature gradient.

In an opposite direction, if the environmental temperature in contact with the body portion containing heat exchange vasculature is then gradually increased, the blood flow in the area of the body and the heat transfer away from the body increases significantly and suddenly at a temperature higher than the vasoconstriction temperature. It is important to note, however, that when the environmental temperature is decreased and causes vasoconstriction, and then increased and causes vasodilation, that the transition to vasodilation typically occurs at a higher temperature than the transition to vasoconstriction, such that the transition between vasoconstriction and vasodilation is not identically reversible. Therefore, the transition from vasoconstriction to vasodilation, and from vasodilation to vasoconstriction, occurs at a different temperature range depending on the initial condition(s), an effect generally referred to as "hysteresis".

To achieve relatively large heat transfer between the body portion containing heat exchange vasculature and the environment, the temperature of the environment in contact with the body portion is desirably at a temperature or range of temperatures just above the vasoconstriction temperature of the body portion, i.e., the temperature associated with the transition from vasodilation to vasoconstriction. This is the temperature at which the temperature gradient between the body portion and the environment is greatest and vasoconstriction is not present, thereby allowing increased heat transfer from the body core. Such teaching is presented in U.S. patent application Ser. No. 09/839,590 entitled Methods and Devices for Extracting Thermal Energy from the Body Core of a Mammal. Yet, the application teaches no means of achieving the desired result outside of applying a thermal medium at a specified temperature.

In contrast, to effect controlled thermomanipulation in one method according to the invention, in order to determine an optimal heat transfer temperature or temperature range of the environment in contact with a heat transfer surface of a mammal's body, the temperature at which vasoconstriction of the body portion occurs is actually determined. The vasoconstriction temperature can be determined by decreasing the environmental temperature from a temperature above the vasoconstriction temperature, to a temperature below the vasoconstriction temperature. For example, the vasoconstriction temperature can be determined by indirectly or directly detecting vasoconstriction at or near the skin surface while decreasing the environmental temperature and noting at which temperature (or range) vasoconstriction occurs. Because the vasodilation temperature is generally greater than the vasoconstriction temperature, if the environmental temperature is initially below the vasoconstriction temperature, the environmental temperature is desirably increased to a temperature above the vasodilation temperature before it is decreased to a temperature below the vasoconstriction temperature to account for the hysteresis effect. The optimal or maximum heat transfer temperature or temperature range of the environment will be the temperature range just above the vasoconstriction temperature or the temperature where the transition to vasoconstriction begins.

Once the optimal heat transfer temperature or temperature range is determined, the environmental temperature in contact with the body portion containing heat exchange vasculature can be set to or near the optimal heat transfer temperature to increase heat transfer from the body to the environment, thus cooling the core body more quickly than at higher or lower temperatures merely representing a guess at an optimal temperature setting.

Methods and devices for determining and using the optimal heat transfer temperature to cool the core body of mammals are provided in greater detail below. In the present methods, the optimal heat transfer temperature is determined, at least in part, on the presence or absence of vasoconstriction in the area of a body portion containing heat exchange vasculature. The core body temperature of the mammal may then be reduced by placing the body portion in an environment at the optimal heat transfer temperature. Further, the temperature where vasoconstriction occurs and the optimal heat transfer temperature may be reduced by the application of heat to various body portions, or other means, to increase the rate of core body cooling. For example, the rate of core body cooling may be increased by the use of negative pressure around the area of a body portion containing heat exchange vasculature in order to distend the venous plexuses, thus increasing the blood volume available for heat transfer.

Various methods and devices may be used for determining a characteristic associated with vasoconstriction or vasodilation in a body portion. In one exemplary method for determining whether a body portion is in a vasoconstriction or vasodilation state, the body portion is monitored by measuring blood flow in the particular body portion. Normally, when body and/or environmental temperatures are high, the dilation of certain blood vessels favors high blood flow to these surfaces, and as environmental and/or body temperatures fall, vasoconstriction reduces blood flow to these surfaces and minimizes heat loss to the environment. As such, measuring the blood flow rate in a body portion provides a measure of whether the body portion is in a state of vasoconstriction or vasodilation.

In one exemplary method for measuring vasoconstriction or vasodilation, blood flow in the body portion is measured and monitored by laser Doppler blood flowmetry. Laser Doppler measurement of the blood flow in a body portion provides a measure of whether the body portion is in a state of vasoconstriction or vasodilation, since changes in blood flow rate are measured. In one example, a laser Doppler imager integrated into a heat exchange device and directed toward the palm, a finger, or other body portion is used to measure changes in blood flow rate through the body portion.

Alternatively, vasoconstriction or vasodilation may be monitored by measuring the volume of a body portion. It is commonly understood that vasodilation coincides with a greater body portion volume than observed during vasoconstriction owing to increased blood volume within the body portion during vasodilation. As such, a physical change in the volume of a body portion can be correlated to a condition of vasodilation or vasoconstriction. One example of measuring the volume of a body portion would be to immerse the body portion in a fluid medium. Any changes in the body portion volume would be registered by a change in the volume of fluid medium displaced by the body portion. Or, it may be measured by an impedance-type sensor.

Alternatively, vasoconstriction or vasodilation may be monitored by measuring the heat transfer of a body portion. For example, the heat transfer of a body portion is tested by measuring the presence or absence of a temperature gradient when measuring the temperature difference, e.g., between a finger and the corresponding forearm of an arm. The absence of a temperature gradient (indicative of heat transfer to the finger) correlates with a condition of vasodilation in the finger, while a higher temperature in the forearm than in the finger (indicative of no heat transfer to the finger) correlates with a condition of vasoconstriction.

Alternatively, vasoconstriction or vasodilation may be monitored by measuring the heat flux at the skin surface. For example, the heat flux at the skin surface is tested by placing a temperature sensing device between the skin surface and a cooling object in contact with the skin's surface. The temperature at this sensing device will indicate vasoconstriction or vasodilation. A temperature higher than that of the cooling object will indicate vasodilation while a temperature close to that of the cooling object will indicate vasoconstriction because the skin surface will be cooler.

Alternatively, vasoconstriction or vasodilation is monitored by measuring light absorption of a portion of the body. For example, light absorption can be detected using the technique of plethysmography or through use of an infrared pulse oximeter.

Alternatively, vasoconstriction or vasodilation may be monitored by measuring the temperature of the body of a mammal. Any convenient temperature sensing means may be employed, where suitable means include but are not limited to: thermocouples, thermosistors, microwave temperature sensors, and the like. The position and nature of the temperature sensing devices generally depends on the body portion being tested.

Temperature measurement may involve monitoring the core body temperature of a mammal. By core body is meant the internal body region or portion of the mammal, as opposed to the surface of the mammal. Specific core body regions of interest are the core body region of the head, e.g., the deep brain region, and the core body region of the trunk of the mammal, e.g., the thoracic/abdominal region of the mammal. For detecting the core body region temperature of the head, sensor locations of interest include: the auditory canal (tympanic), the oral cavity, and in the case of microwave detection, anywhere on the surface of the head to measure underlying temperature. For detecting thoracic/abdominal core body temperature, sensor locations include: the esophagus, the rectum, the bladder, the vagina, and in the case of microwave detection, anywhere on the surface of the body to measure the underlying temperature.

Alternatively, vasoconstriction or vasodilation may be monitored by measuring the skin temperature of a mammal. For detecting the skin temperature of a mammal, the simple empirical nursing methodology of holding the hand to test for warmth or coldness can be used. In practicing this method of skin temperature measurement, a warm hand is generally associated with vasodilation, while a cold hand is associated with vasoconstriction. The temperature of the skin can also be detected using sensors such as thermocouples, thermoresistors, microwave temperature sensors, temperature sensitive liquid crystals, and other temperature measuring devices. Placement of temperature sensors on the skin surface could be at the site of heat transfer or other locations, or a combination of locations. In one example, vasoconstriction or vasodilation may be monitored by measuring changes in skin surface temperature or heat flow from the body across local skin surface area overlying heat exchange vascular structures.

As for these means of monitoring vasoconstriction or vasodilation through temperature observation, note-that only detecting temperature at the location of heat transfer provides a direct measure of local vasoconstriction. However the monitoring is effected (even—for example—by a combination of any two or more of the above approaches), by controlling vasoconstriction or vasodilation in a body portion of a mammal, the vasoconstriction temperature and the heat transfer temperature can be lowered to increase the temperature gradient between the area of the body containing heat exchange vasculature and the environment, thus increasing heat transfer and facilitating core body cooling.

In an aspect of the invention, vasoconstriction or vasodilation is controlled through thermoregulatory sensory manipulation or "fooling the brain thermostat." Certain aspects of such manipulation are provided in U.S. Pat. No. 6,602,277 to Grahn, et al., entitled, "Methods and Devices for Manipulating the Themoregulatory Status of a Mammal," others aspects are refined herein as will be apparent to one with skill in the art. All such aspects may find use according to the improvements offered by aspects of the present invention.

In any case, it is generally accepted that the brain of a mammal, particularly the Pre-Optic Anterior Hypothalamus (POAH), plays a key role in regulating the temperature of body portions in mammals, essentially playing the role of a "thermostat." In practicing exemplary method, heat transfer away from a body portion is achieved by manipulating the temperature of blood flow to the brain or by changing the skin temperature of the body (including the head, torso, face, and neck) in order to manipulate (i.e. "fool") the POAH, by inducing it to trigger vasoconstriction or vasodilation in the body portion allowing controlled heat transfer away from the portion. It has further been appreciated that other stimuli, such as humidity stimulus, may be applied to the body portion alone or in conjunction with changing the skin temperature.

Manipulating the temperature of blood flow to the brain could be achieved by, for example, thermal wraps around the neck or face. Heat and/or humidity introduced through such wraps is one way to affect the POAH such that vasodilation is induced and heat transfer away from a body portion such as an arm or leg occurs. Alternatively, humidity may be applied through such wraps alone or in conjunction with changing the skin temperature.

Alternatively, in practicing the subject method, manipulating the temperature of blood flow to the brain could be achieved through use of a suit covering portions of the body and having heating and cooling components and/or humidity controlling components. Exemplary sensory manipulation devices are described below in greater detail (see, e.g., FIGS. 4a–4h).

Alternatively, vasoconstriction or vasodilation could be controlled through application of a surface treatment. For example, vasoconstriction is induced in a body part through topical application of Capsaicin (derived from peppers), poison oak, BEN-GAY, a variety of liniments, a topical irritant, or other suitable chemical and/or biological materials.

Alternatively, vasoconstriction or vasodilation could be controlled through providing one or more pre-selected visual stimuli. In practicing the subject methods, vasoconstriction could be induced, for example, by triggering the "fight or flight" response through visual stimulation of a mammal.

Alternatively, vasoconstriction or vasodilation could be controlled through delivery of drugs producing vasoconstriction or vasodilation. For example, drugs may be delivered through injection, inhalation, topically, orally, through the nasal passages, and the like.

In another aspect, heat transfer away from a body portion may be facilitated by applying a negative pressure condition to a portion of the body in order to lower the vasoconstriction temperature and/or increase vasodilation in the body portion. In practicing the exemplary methods, the negative pressure conditions may be provided using any convenient protocol. In many embodiments, the negative pressure conditions are provided by enclosing a body portion of the mammal in a sealed enclosure, where the pressure is then reduced in the sealed enclosure thereby providing the desired negative pressure that includes a target heat exchange surface. In many examples of the present methods and systems, the portion that is sealed includes an arm or leg, or at least a portion thereof, e.g., a hand or foot. The nature of the enclosure will vary depending on the nature of the appendage to be enclosed, where representative enclosures include gloves, shoes/boots, or sleeves (see, e.g., FIGS. 2 and 3).

Negative pressure includes conditions where a pressure lower than ambient pressure under the particular conditions in which the method is applied, e.g., 1 ATM at sea level. The magnitude of the decrease in pressure from the ambient pressure under the negative pressure conditions in one example is at least about 20 mmHg, preferably at least 30 mmHg, and more preferably at least about 35 mmHg, where the magnitude of the decrease may be as great as 85 mmHg or greater, but preferably does not exceed about 60 mmHg, and more preferably does not exceed about 50 mmHg. When the method is performed at or about sea level, the pressure under the negative pressure conditions generally may range from about 740 to 675 mmHg, preferably from about 730 to 700 mmHg and more preferably from about 725 to 710 mmHg.

In practicing the exemplary methods, the negative pressure conditions during contact with the skin of a subject may be static/constant or variable. Thus, in certain examples, the negative pressure is maintained at a constant value during contact of the surface with the low temperature medium. In yet other examples, the negative pressure value is varied during contact, e.g., oscillated. Where the negative pressure is varied or oscillated, the magnitude of the pressure change during a given period may be varied and may range from about 85 to 40 mmHg, and preferably from about 40 to 0 mmHg, with the periodicity of the oscillation ranging from about 0.25 sec to 10 min, and preferably from about 1 sec to 10 sec.

Further discussion of suitable vacuum/negative pressure approaches are described in the U.S. Pat. No. 6,602,277 noted above as well as U.S. Pat. No. 5,683,438 to Grahn and PCT Patent Application PCT/US02/09772 and U.S. patent application Ser. Nos. 09/839,590 and 09/877,407 to Grahn, et al.—all of which are incorporated herein by reference in their entireties. Any other details informing the operation of the present invention may be drawn from one or more of these four sources, or be provided by application of the talents of one with ordinary skill in the art.

Embodiments

Turning now to FIG. 1, it illustrates a diagram of an exemplary system architecture for the methods described herein. The exemplary system may include a systems controller 4, pressure source 5, thermal exchange engine 6, thermoregulatory sensor manipulation device controller 7, sensory manipulation device 8, hand enclosures 2 and 12 including conductor 1, foot enclosure 13, plumbing and/or electrical connections 3, interface specific sensors 10, and body temperature sensors 11.

Systems controller 4 provides and receives signals from the various system components to achieve controlled heat transfer from at least a portion of a body of mammal 9 according to the various methods described. The systems controller 4 may include a unit having a suitably programmed microprocessor or the like, including algorithms or program logic for various heating and cooling protocols and schedules as described in detail below. The algorithms may be carried out through software, hardware, firmware, or any combination thereof. The programming can be recorded on computer readable media, (e.g., any medium that can be read and accessed directly by a computer). Such media include, but are not limited to: magnetic storage media, such as floppy discs, hard disc storage medium, and magnetic tape; optical storage media such as CD-ROM; electrical storage media such as RAM, ROM, or an EPROM; and hybrids of these categories such as magnetic/optical storage media. Any such medium (or other medium) programmed (in full or in part) to operate according to the subject methodology also forms an aspect of the invention.

Systems controller 4 is in communication with a thermal exchange engine 6, which is capable of heating or cooling a heat exchange medium (not shown) in communication with the conductor 1 located within sealed enclosure 2. The heat exchange medium provided may communicate thermally with at least a portion of the mammal 9 and with at least a portion of the conductor 1. In certain examples, the heat exchange medium is comprised of a fluid such as water, oil, and the like. In other examples the heat exchange medium may include gas or air. In further examples, the heat exchange medium may include solid-state heating or direct electrical heating. Additionally, the systems controller is in communication with a reservoir (not shown) for containing a supply of heat exchange medium.

Systems controller 4 is further in communication with a pressure source 5 capable of producing negative pressure conditions in the sealed enclosure 2. The thermal exchange engine 6 and the pressure source 5 are in communication with the conductor 1 and the sealed enclosure 2 respectively, through plumbing and/or electrical connections 3 capable of conducting heat exchange medium and pressure separately or in combination. The conductor 1 provides an interface between a body portion of a mammal 9 and the heat exchange medium in order to heat or cool the body portion of mammal 9. The conductor 1 may include any of a number of suitable materials for transferring heat. Examples of such materials are metals including, but not limited to, aluminum, stainless steel, or titanium. In one example, conductor 1 is disposed within sealed enclosure 2 in which the body portion is maintained under negative pressure conditions as described above in detail.

Conductor 1 and sealed enclosure 2 together make up either a hand interface 12 or a foot interface 13. In one example of the present system, the hand interface 12 encloses the arm or hand of mammal 9. In another example of the present system, the foot interface 13 encloses the leg or foot of mammal 9. In yet another example of the present system, the enclosed body portion includes both arms or hands, both legs or feet, or any combination of the preceding body portions of mammal 9. The hand interface 12 and the foot interface 13 are described below in detail, and shown in FIGS. 2 and 3 respectively.

The systems controller 4 disclosed in FIG. 1 is additionally in communication with the thermoregulatory sensory manipulation device controller 7 that is further in communication with a thermoregulatory sensory manipulation device 8. The thermoregulatory sensory manipulation device 8 is capable of inducing, for example, mild hypothermia for controlling a mammal's 9 thermoregulatory response through manipulation of the sensing mechanisms of the brain's (or body's) thermostat. Suitable thermoregulatory sensory manipulation devices may include, but are not limited to, interfaces designed to deliver temperature and/or humidity stimulus to the following combinations of body portions, some of which are illustrated in FIGS. 4*a–h*: the entire body skin surface (FIG. 4*a*); head, shoulders, chest, back, torso and arms (FIG. 4*b*); head shoulders, chest, back and arms (FIG. 4*c*); head shoulders, chest and back (FIG. 4*d*); shoulder, chest, back and arms (FIG. 4*e*); shoulders, chest, back and torso (FIG. 4*f*); chest back torso and legs (FIG. 4*g*); torso and legs (FIG. 4*h*); head and shoulders; head and neck; head; full face; nose; mouth; nose and mouth; nose and sinuses; and ears. It should be recognized that various other sensory manipulation devices not shown may be used in accordance with the above methods.

Systems controller 4 disclosed in FIG. 1 is additionally in communication with any of a number of direct or interface specific sensors 10 disposed within or in conjunction with the conductor 1 as described below and shown in detail in FIG. 2. The interface specific sensors 10 provide the systems controller 4 with feedback, e.g., characteristics associated with vasoconstriction or vasodilation, such as the relative state of blood flow indicating vasoconstriction or-vasodilation, of the body portion enclosed. Interface specific sensors 10 may include but are not limited to: laser Doppler blood flow sensing; bio-impedance blood flow sensing; heat flux sensing; interface temperature sensing; skin temperature sensing; pressure sensing; body portion volume sensing; energy transfer sensing; EKG/ECG or any of the methods disclosed above. Exemplary methods for interpreting and using feedback from the interface specific sensors 10 in order to maintain or achieve vasodilation to achieve controlled heat transfer from the body of a mammal are provided below.

Systems controller 4 may additionally be in communication with any of a number of systemic body temperature measuring sensors 11 disposed appropriately on or within the body of the mammal 9. The systemic body temperature sensors 11 provide the systems controller 4 with feedback regarding the core body temperature of the mammal 9, which is desired for systems controller 4 to carry out optional portions of exemplary methods detailed below. The systemic body temperature sensors 11 could include but are not limited to: tympanic temperature sensors; esophageal temperature sensors; and core body temperature sensors including but not limited to the methods disclosed above.

Figure 2:
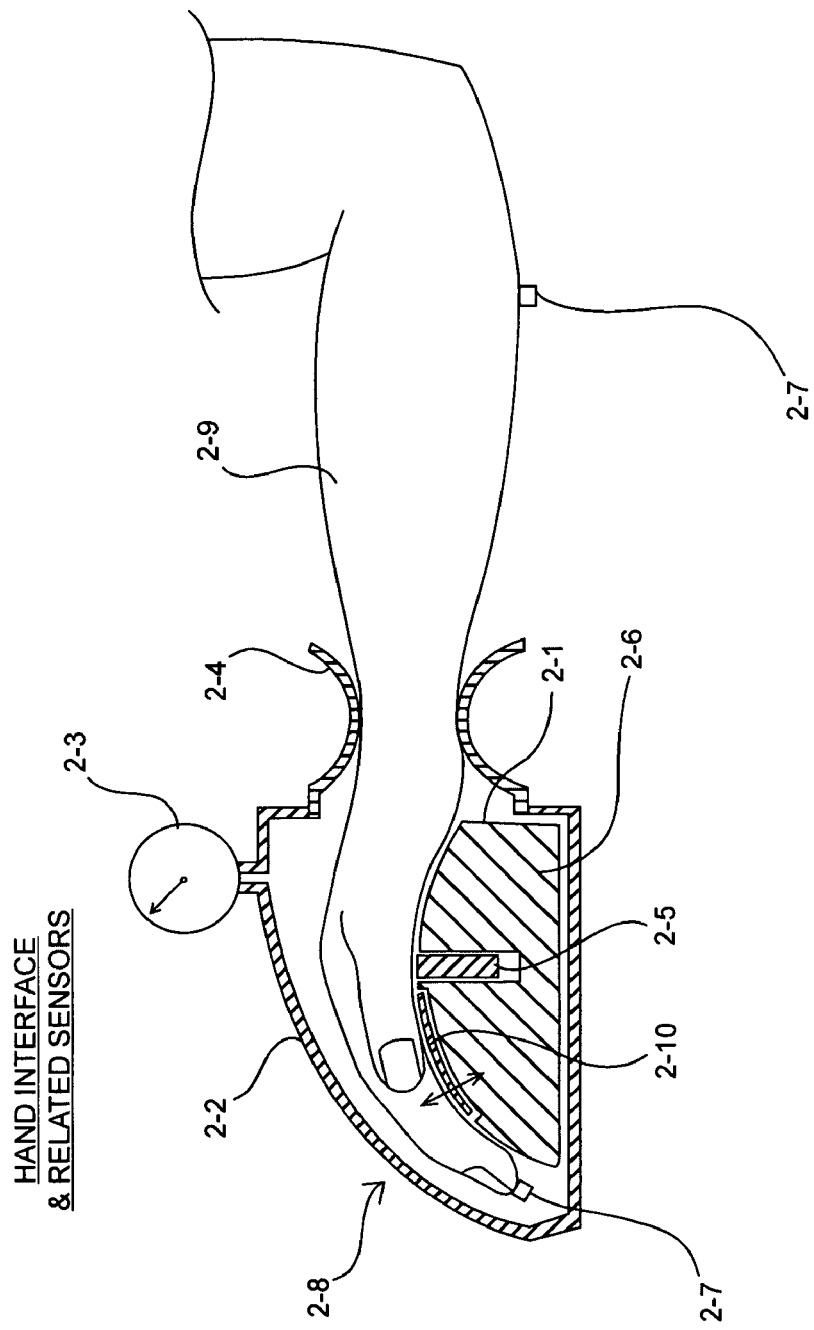
FIG. 2 illustrates an exemplary hand interface for heat transfer.

FIG. 2 includes a diagram illustrating details of an exemplary hand interface 2-8 that may be used with the system architecture of FIG. 1. The purpose of the hand interface 2-8 includes providing a physical heat exchange surface between the hand of a mammal 2-9 and the conductor 2-1 under conditions of negative pressure. The hand interface 2-8 is designed to provide temperature and/or humidity stimulus to the hand of mammal 2-9. Additionally, the hand interface 2-8 enables monitoring and/or manipulation of vasoconstriction or vasodilation through various sensors that are in communication with the systems controller (FIG. 1). Under the guidance of the systems controller the hand interface 2-8 facilitates controlled heat transfer from the body of mammal 2-9. Another exemplary hand interface or module that may be used is described in U.S. patent application Ser. No. 09/878,129, entitled, "Methods and Devices for Manipulating Thermoregulatory Status of a Mammal," which is hereby incorporated by reference in its entirety as if fully set forth herein.

The hand interface 2-8 includes a conductor 2-1 that serves as a thermal exchange interface disposed within the sealed enclosure 2-2 and having a configuration that accommodates contact between the palm and/or fingers of the mammal 2-9 and the conductor 2-1. The sealed enclosure includes a seal cuff 2-4 and a pressure sensor 2-3 that enables maintenance and monitoring of negative pressure conditions within enclosure 2-8. It should be recognized, however, that an exemplary hand interface 2-8 need not include an enclosure capable of maintaining a negative pressure. For example, hand interface 2-8 may include merely a thermal exchange interface or conductor 2-1 for the hand to contact without an enclosure.

The hand interface 2-8 may accommodate any of a number of sensing components. For example, as shown in FIG. 2, a heat flux and interface temperature sensor 2-10 can be disposed between the hand of mammal 2-9 and the conductor 2-1. Additionally, a laser Doppler or absorbing light blood flow sensor 2-5 could be disposed within or proximal to the conductor 2-1 for measuring blood flow in the hand of mammal 2-9. Additionally, a heat energy transfer sensor 2-6 could be disposed within the conductor 2-1 for measuring the transfer of heat energy between the hand of mammal 2-9 and the conductor 2-1. The hand interface 2-8 could also accommodate a skin temperature probe adapted to measure a temperature difference between portions of mammal 2-9 (e.g., a change in temperature from the forearm-to-finger tip), and bio-impedance sensors 2-7 as described above for monitoring blood flow in the hand of mammal 2-9.

Figure 3:
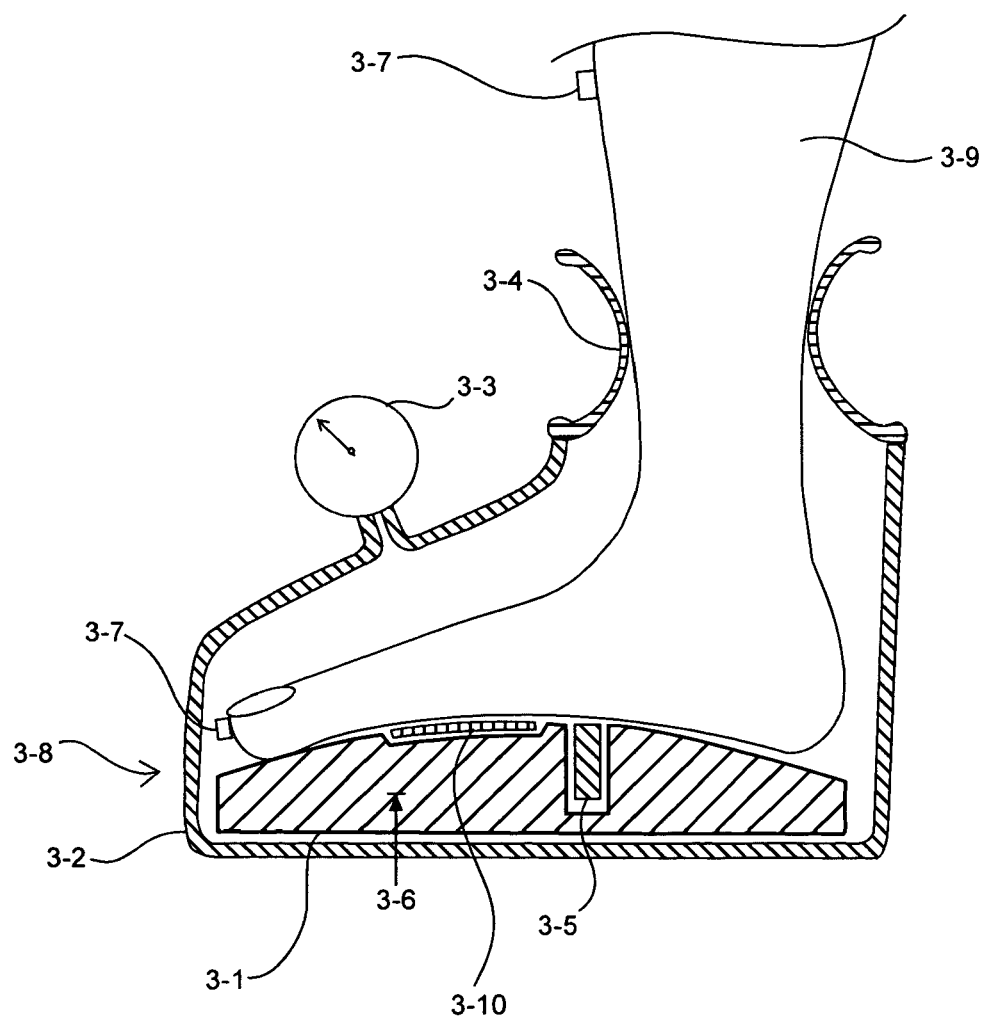
FIG. 3 illustrates an exemplary foot interface for heat transfer.
Figure 4B:
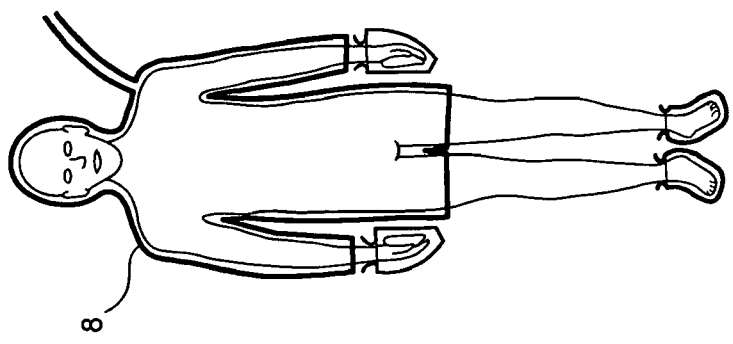
FIGS. 4A–4H illustrate various exemplary configurations of thermoregulatory sensory manipulation devices.
Figure 4A:
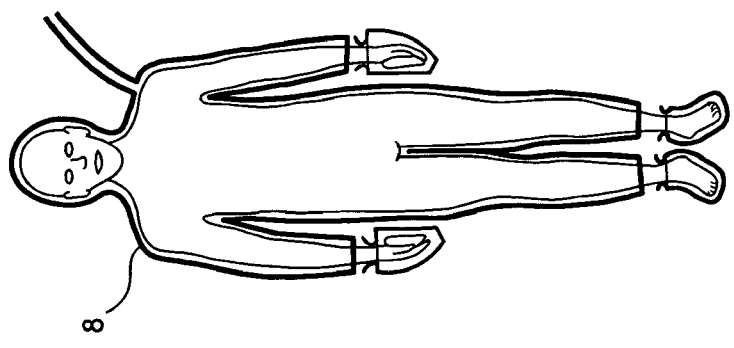
Figure 4D:
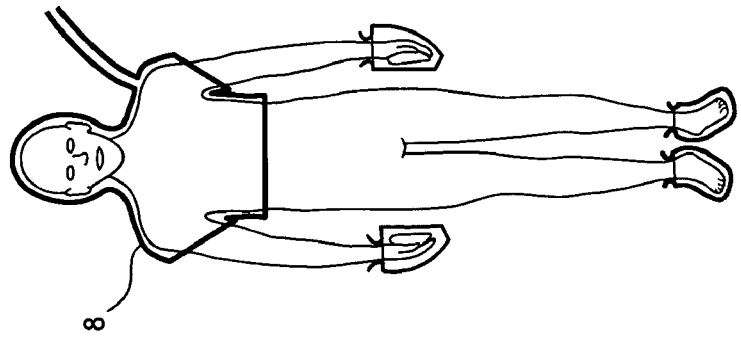
Figure 4C:
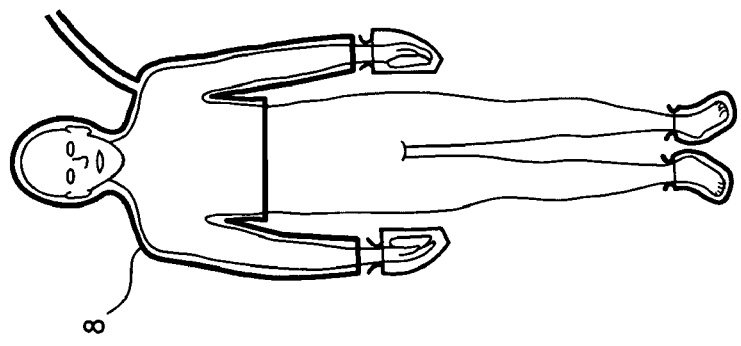
Figure 4F:
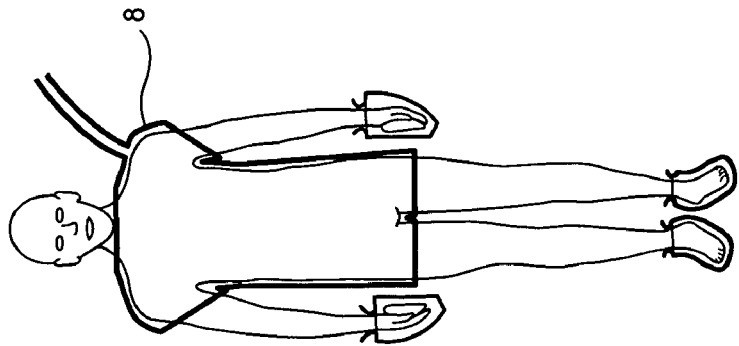
Figure 4E:
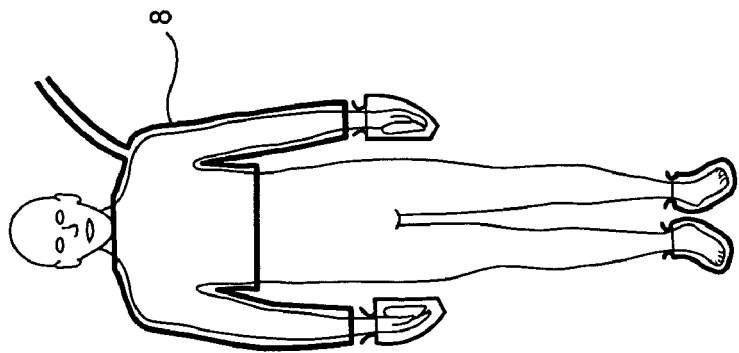
Figure 4H:
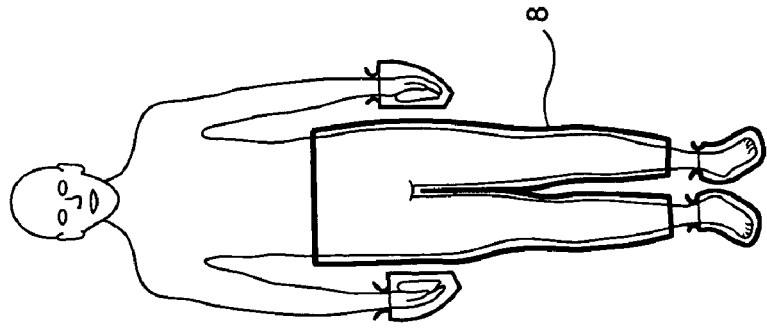
Figure 4G:
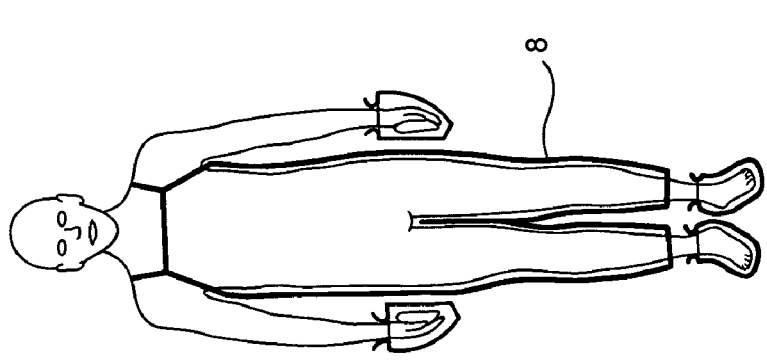

FIG. 3 includes a diagram illustrating details of an exemplary foot interface 3-8 for a foot of mammal 3-9. The foot interface 3-8, like that of the hand interface described above, provides a physical heat exchange surface between the foot of mammal 3-9 and the conductor 3-1 under conditions of negative pressure. The foot interface is designed to provide temperature and/or humidity stimulus to the foot of a mammal. Additionally, as in the case of the hand interface, the foot interface enables monitoring and manipulation of vasoconstriction or vasodilation through various sensors that are in communication with the systems controller (see, FIG. 1). Under the guidance of the systems controller the foot interface facilitates controlled heat transfer from the body of mammal 3-9.

The foot interface 3-8 includes a conductor 3-1 that serves as a thermal exchange interface disposed within the sealed enclosure 3-2 and having a configuration that accommodates contact between the sole of the foot and/or toes of the mammal 3-9 with the conductor 3-1. The sealed enclosure includes a sealed cuff 3-4 and a pressure sensor 3-3 that enable maintenance and/or monitoring of negative pressure conditions as described above. Similar to the hand interface, it should be recognized that the exemplary foot interface 3-8 need not include an enclosure capable of maintaining a negative pressure.

The foot interface 3-8 may accommodate any of a number of sensing components. For example, as shown in FIG. 3, a heat flux and interface temperature sensor 3-10 can be disposed between the foot of mammal 3-9 and conductor 3-1. Additionally, a laser Doppler or absorbing light blood flow sensor 3-5 could be disposed within or proximal to the conductor 3-1 for measuring blood flow in the foot of a mammal. Additionally, a heat energy transfer sensor 3-6 could be disposed within the conductor for measuring the transfer of heat energy between the foot of mammal 3-9 and the conductor 3-1. The foot interface 3-8 could also accommodate a skin temperature probe adapted to measure a temperature difference between portions of mammal 3-9 (e.g., a change in temperature from the leg-to-toe tip), and bio-impedance sensors 3-7 for monitoring blood flow in the foot of mammal 3-9 as described above.

Figure 5:
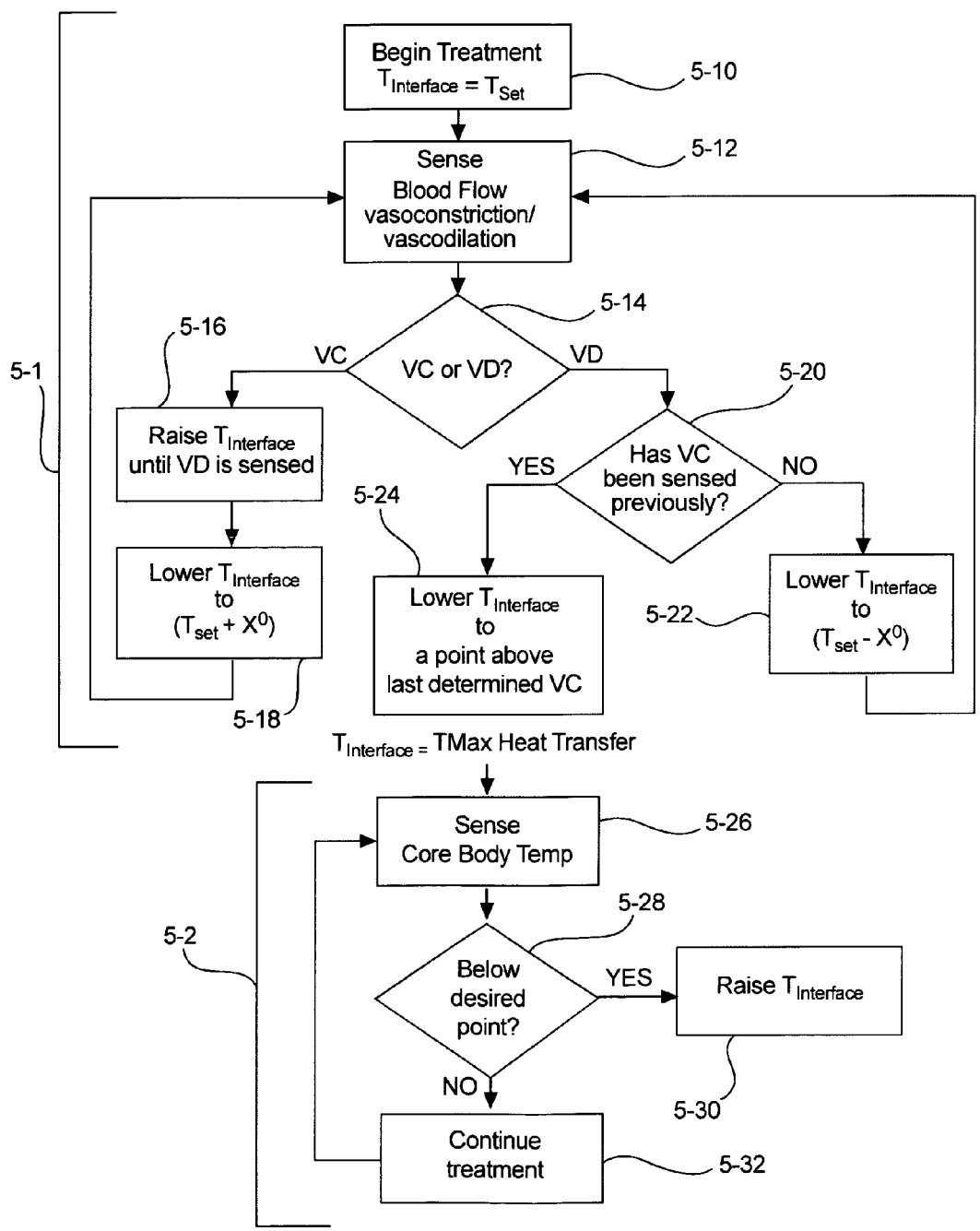
FIG. 5 illustrates an exemplary control method for heat transfer.
Figure 6:
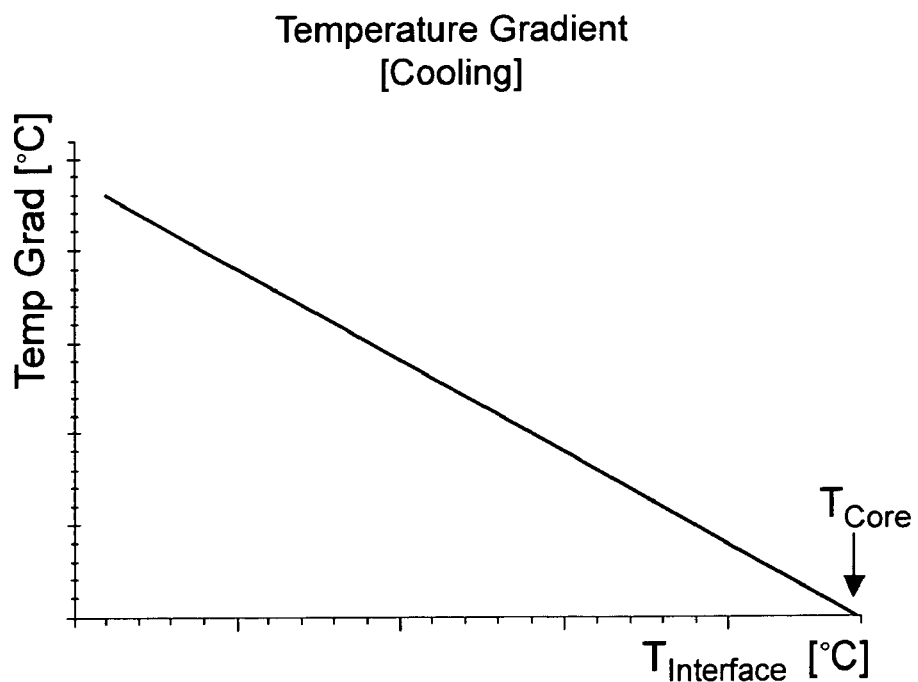
FIG. 6 illustrates an exemplary graph of interface temperature versus temperature gradient.

In one exemplary method for effecting controlled heat transfer from the body of a mammal, the driving force includes heat transfer between some portion of the mammal's body, e.g., a skin surface overlying the referenced heat exchange vasculature, and a thermal interface or conductor (described above and shown in FIGS. 1–3). FIGS. 6–11 illustrate more clearly how the exemplary methods and systems described herein effect an optimal heat transfer from the body core to the environment and FIG. 5 illustrates one exemplary method for the system architecture to effectuate increased heat transfer from a mammal. FIG. 6 includes a graph depicting a temperature gradient representing the temperature difference between a mammal's body core temperature ($T_{core}$) in ° C. and the interface temperature ($T_{interface}$) in ° C. The Y-axis represents an increasing temperature gradient ($T_{core}-T_{interface}$) in ° C. while the X-axis represents increasing $T_{interface}$ in ° C. As shown in FIG. 6, when the difference between $T_{core}$ and $T_{interface}$ reaches zero (i.e., they are equal) the temperature gradient no longer exists and heat transfer does not occur (see arrow marking $T_{core}$). Conversely, the temperature gradient increases as $T_{interface}$ is increasingly lower than $T_{core}$.

Figure 7:
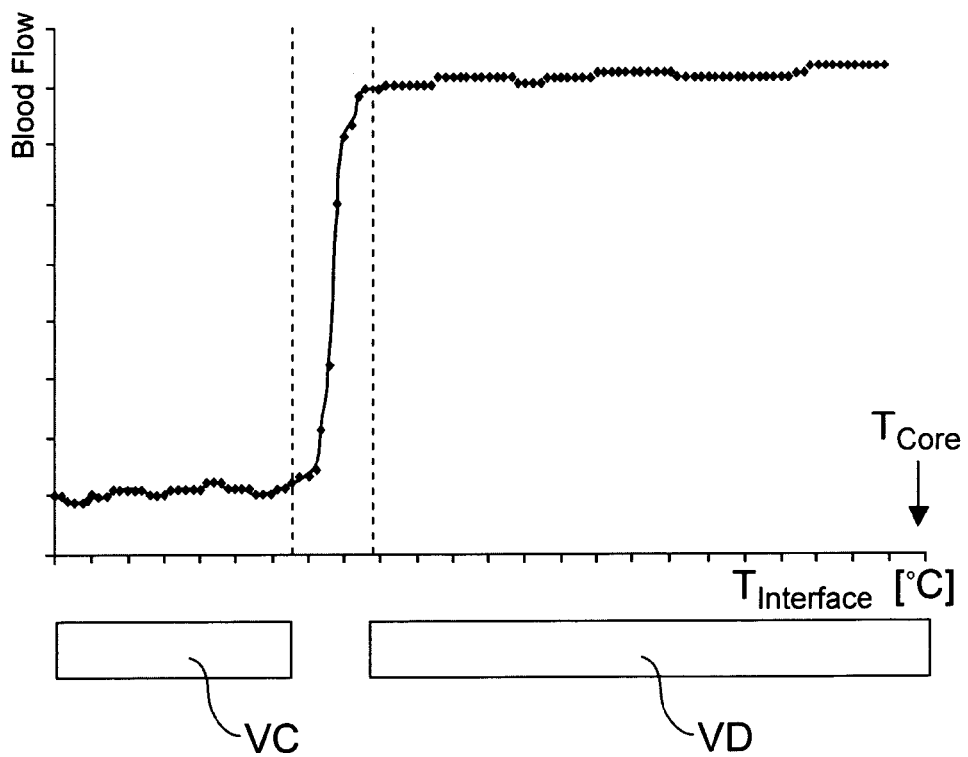
FIG. 7 illustrates an exemplary graph of interface temperature versus blood flow.

For each individual mammal, vasoconstriction of blood flow within a body portion occurs below a certain measurable temperature range while vasodilation occurs at some point above that temperature range. FIG. 7 illustrates this principle by relating increasing levels of blood flow in a body portion on the Y-axis to increasing temperatures of $T_{interface}$ on the X-axis. As shown in FIG. 7, relatively low blood flow or vasoconstriction (shown as bar VC below the X-axis) corresponds to a lower range of $T_{interface}$ that extends up to a zone of transition and culminates in a range of relatively high blood flow corresponding to vasodilation (shown as bar VD below the X-axis).

Figure 8:
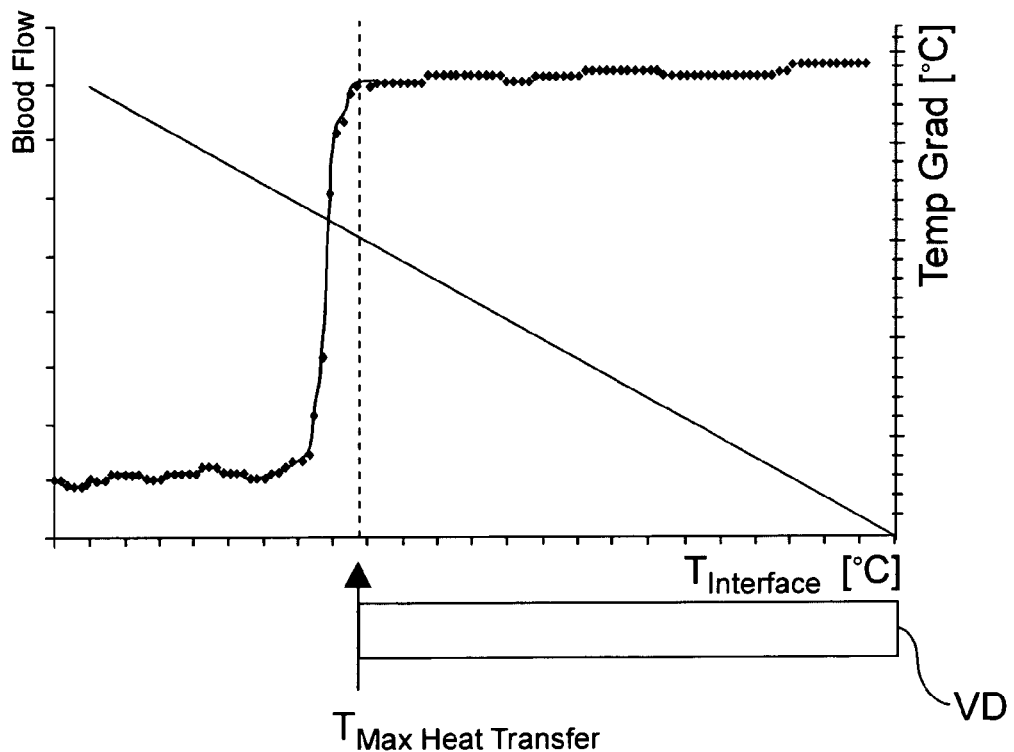
FIG. 8 illustrates an exemplary graph of interface temperature versus blood flow.

One advantage of the exemplary methods and systems described herein includes that they relate to both of the foregoing concepts presented in FIGS. 6 and 7. Namely, the systems and methods enable increased heat transfer ($T_{Max\ Heat\ Transfer}$) from the body of a mammal by determining the lowest $T_{interface}$ at which vasodilation can be maintained. As illustrated in FIG. 8, heat transfer can be related as a function of temperature gradient times blood flow. The graph in FIG. 8 superimposes the two graphs of FIGS. 6 and 7 to more clearly illustrate that $T_{Max\ Heat\ Transfer}$ occurs at the lowest $T_{interface}$ that supports vasodilation, since higher $T_{interface}$ values correlate to diminishing temperature gradients and concomitant reduced cooling effect.

Figure 9:
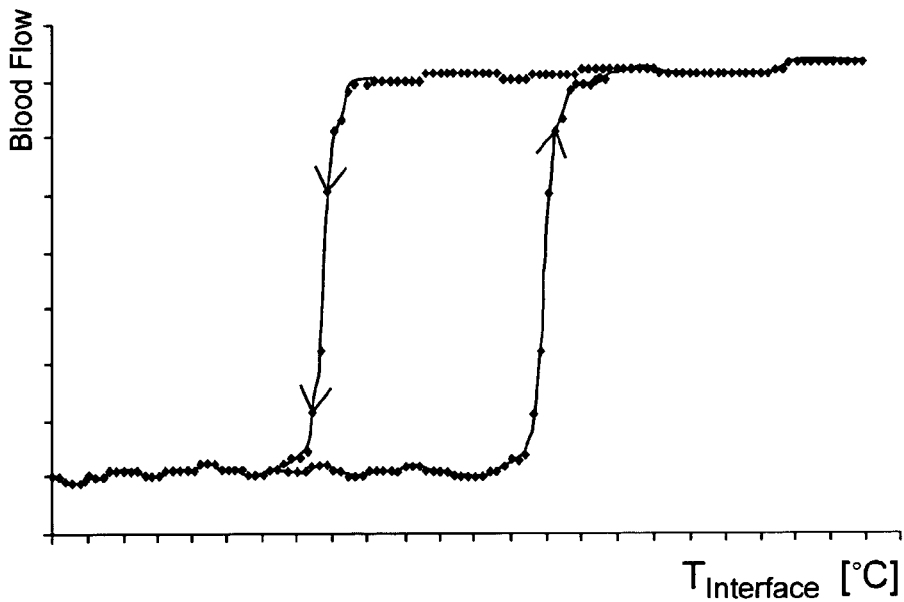
FIG. 9 illustrates an exemplary graph of interface temperature versus blood flow including a transition between vasoconstriction and vasodilation.

An additional advantage of the exemplary methods and systems includes that they address the hysteresis phenomenon generally found in the opposing transitions between vasoconstriction to vasodilation, and vasodilation to vasoconstriction. Disclosed in FIG. 9 is an exemplary illustration of the phenomenon of hysteresis as it relates to blood flow and $T_{interface}$. FIG. 9 shows increasing blood flow on the Y-axis and $T_{interface}$ on the X-axis to illustrate that the transitions between vasoconstriction and vasodilation are not identically reversible with respect to $T_{interface}$ values. Depending on the initial condition (i.e., vasoconstriction or vasodilation initially) the transition occurs at a different temperature range. Particularly, the transition from vasoconstriction to vasodilation (FIG. 9 plot marked with upward pointing arrows) occurs at a $T_{interface}$ range that is higher than that for the transition from vasodilation to vasoconstriction (FIG. 9 plot marked with downward pointing arrows).

With the foregoing as a foundation establishing some of the advantages and principles relating to the present methods, an exemplary method for heat transfer and controlling a system may now be discussed in greater detail. Disclosed in FIG. 5 is a flow chart showing an exemplary method that guides the systems controller (described above and shown in FIG. 1) in order to effect controlled heat removal from the body of a mammal. A system, e.g., having an appropriately programmed algorithm, program logic, or the like, begins with a starting value ($T_{set}$) that equals the starting value for $T_{interface}$ (described above). The algorithm may further include two main components or functions, the first being focused on characteristics relating to vasoconstriction and/or vasodilation, e.g., blood flow monitoring and manipulation, and the second focused on core body temperature monitoring and manipulation.

The first portion of the method corresponds to the sensing of vasoconstriction or vasodilation, e.g., by measuring blood flow, and manipulation of vasoconstriction or vasodilation in a mammal's body part through a thermal interface or conductor (e.g., as described above and shown in FIGS. 1–3) in order to establish and maintain $T_{Max\ Heat\ Transfer}$ (as described above and shown in FIG. 8). Accordingly, as shown in FIG. 5 generally as 5-1, this aspect of the method analyzes data regarding the mammal's state of vasoconstriction or vasodilation, and based on this analysis signals for the manipulation of vasoconstriction or vasodilation or blood flow through incrementally raising or lowering the $T_{set}$ value (e.g., $T_{set}+X°$; $T_{set}-X°$).

Specifically, in block 5-10, the interface temperature begins at a set temperature, $T_{set}$, which may depend on various factors such as the application, body portion, mammal type, and the like. In block 5-12 a measurement of blood flow or other characteristic associated with vasoconstriction or vasodilation in the body portion is sensed. In block 5-14 a determination is then made as to whether the body portion is in a state of vasoconstriction or vasodilation. An initial determination of vasodilation or vasoconstrictions may be made simply by looking at the color of the skin, e.g., on the hand; or by previous measurement of vasodilation or vasoconstriction using any suitable method for measuring vasoconstriction or vasodilation.

If a determination is made that the body portion is in vasoconstriction, the interface temperature is raised in block 5-16 until vasodilation is sensed. The interface temperature, $T_{interface}$, is then lowered in block 5-18 to a temperature greater than the original set temperature, $T_{set}$, in block 5-10, e.g., X° C. greater. The temperature difference may vary depending on the application and testing. A characteristic associated with vasoconstriction or vasodilation is then sensed again in block 5-12 and a determination made as to vasoconstriction or vasodilation in block 5-14.

If a determination is made that the body portion is in vasodilation, the method determines if vasoconstriction has been previously sensed in block 5-20. If not, the interface temperature, $T_{set}$, may be lowered to a temperature below the original set point in block 5-10 and the blood flow or other characteristic sensed again in block 5-12. If vasoconstriction has been previously detected, then the method lowers the interface temperature, $T_{set}$, to a point above the last detected vasoconstriction temperature.

The second, optional, function of the algorithm may include the sensing of the mammal's core body temperature (discussed above and shown in FIG. 1 with regard to body temperature sensors 11) in order to monitor and govern the process of controlled body core heat removal treatment. This function of the method is preferably used in situations where it is desirable to reduce the core body temperature below its normal temperature and the core body temperature is generally more closely monitored. As shown in FIG. 5 as 5-2, this function of the algorithm serves to continuously monitor and govern the effect of heat transfer away from the body part(s), which consequently controls body core heat removal. Particularly, this aspect of the exemplary method takes data regarding the mammal's core body temperature and compares that value to $T_{Max\ Heat\ Transfer}$. Where the core body temperature is found to be at or above the pre-established $T_{Max\ Heat\ Transfer}$ for the mammal, the method provides for treatment to proceed at the present $T_{interface}$ (described above) value. Where the core body temperature is calculated to be below $T_{Max\ Heat\ Transfer}$, the method signals for an increase in $T_{interface}$, and core body temperature data is continuously monitored until it has again reached $T_{Max\ Heat\ Transfer}$. This process may be repeated in a cyclic fashion in order to achieve a goal of controlled heat removal treatment over a period of time.

Specifically, with reference to FIG. 5, the exemplary method proceeds to block 5-26 where the core body temperature is detected by any suitable method. If it is below a desired temperature in block 5-28, the interface temperature is raised in block 5-30. The core body temperature may then be determined again and the interface temperature increased if necessary.

The methods described in FIG. 5 may be carried out by a controller having a suitable algorithm, program logic, and the like. Alternatively, the exemplary method may be carried out by a person, e.g., a doctor, patient, or the like. Further, the method indicates certain events or operations occurring in a certain order. In alternative implementations, the order of certain events and operations may be varied, modified, or removed. Moreover, acts may be added to the described method and still conform to the described implementations. Further, operations described herein may occur sequentially or certain operations may occur in parallel.

Figure 10:
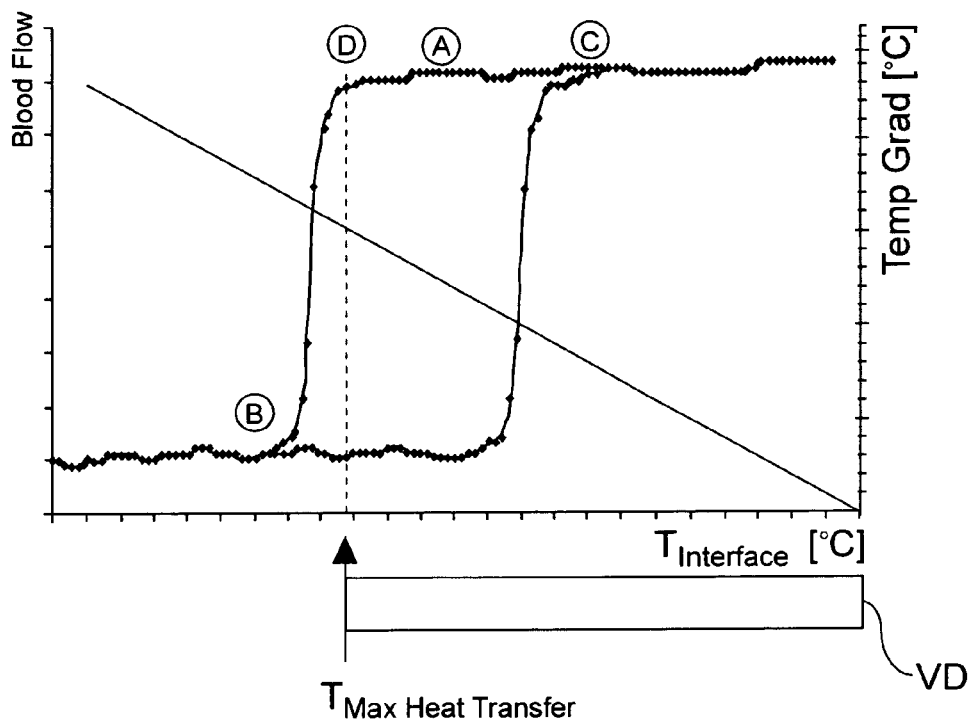
FIG. 10 illustrates an exemplary graph of interface temperature versus blood flow including a transition between vasoconstriction and vasodilation.

An advantage of the exemplary methods and systems includes enabling a heat removal treatment from a starting point of vasoconstriction or vasodilation by accounting for the physiological hysteresis phenomenon discussed above and shown in FIG. 9. For example, FIG. 10 illustrates a graphical representation of the method of FIG. 5 in an instance where vasodilation is initially detected in the body part of a mammal. In this case, from a starting point of vasodilation, the method serves to establish and maintain $T_{Max\ Heat\ Transfer}$ after a condition of vasodilation is initially detected. An exemplary method or subroutine, e.g. 5-1, accounts for the hysteresis phenomenon attendant to the transitions between vasoconstriction and vasodilation and initial conditions. According to the hysteresis phenomenon shown in FIG. 9, the value of $T_{Max\ Heat\ Transfer}$ is lower than the arbitrary value chosen for $T_{set}$. Specifically, starting with point (A) of FIG. 10, where blood flow in a body portion indicates a state of vasodilation, the value of $T_{interface}$ is arbitrarily made equivalent to $T_{set}$. The system controller then incrementally decreases the value of $T_{interface}$ below the initial $T_{set}$ value (e.g., $T_{set}-X°$) until the transition temperature range between vasoconstriction and vasodilation is passed and vasoconstriction is achieved as shown at point (B). The system controller may then increase $T_{interface}$ incrementally above the initial $T_{set}$ value (e.g., $T_{set}+X°$) until the transition temperature range between vasoconstriction and vasodilation is reached as shown at point (C). Lastly, the system controller incrementally decreases the value of $T_{interface}$ to the point of $T_{Max\ Heat\ Transfer}$ as shown at point (D). In summary, this subroutine provides steps that serve to manipulate a mammal's body portion temperature to induce vasoconstriction in order to establish a value for $T_{Max\ Heat\ Transfer}$, followed by re-establishment of vasodilation through raising the value of $T_{interface}$ to some point above $T_{Max\ Heat\ Transfer}$ before finally lowering $T_{interface}$ to the point of $T_{Max\ Heat\ Transfer}$.

Figure 11:
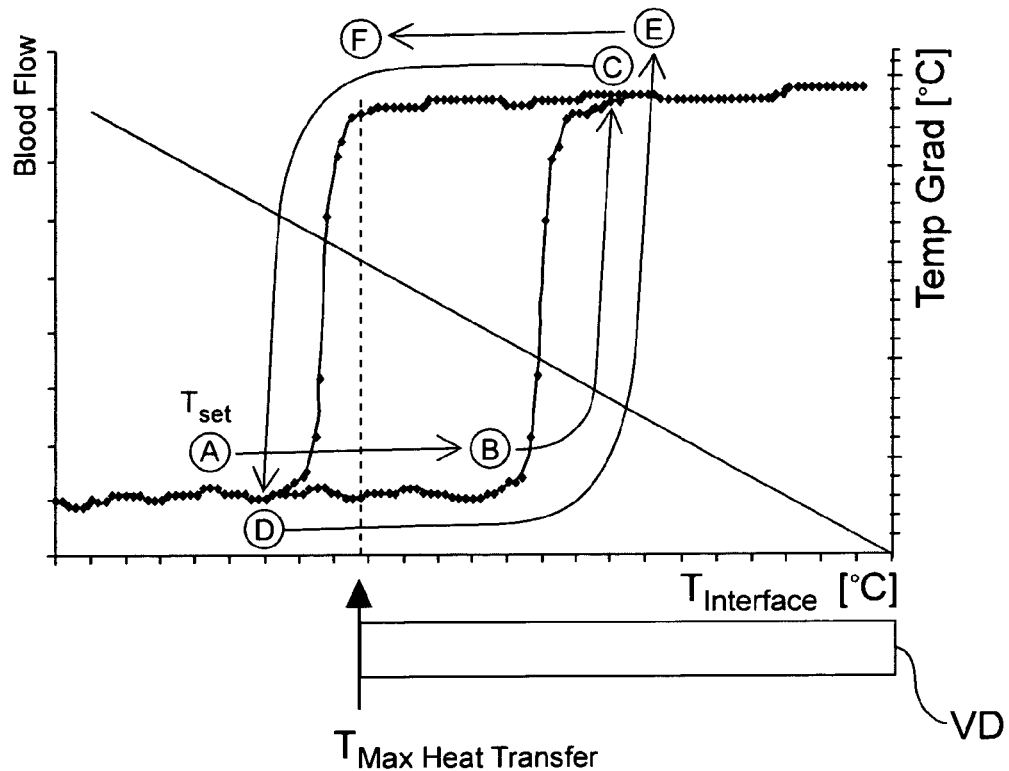
FIG. 11 illustrates an exemplary graph of interface temperature versus blood flow including a transition between vasoconstriction and vasodilation.

FIG. 11 illustrates a graphical representation of the method shown in FIG. 5 for an example where vasoconstriction is initially detected in the body part of a mammal. As disclosed in FIG. 11, the subject subroutine of the algorithm serves to establish and maintain $T_{Max\ Heat\ Transfer}$ while taking into account the hysteresis phenomenon attendant to the subject methods (described above and in FIG. 9). Specifically, starting at point (A) of FIG. 11, where blood flow in a body portion indicates a state of vasoconstriction, the value of $T_{interface}$ is arbitrarily made equivalent to $T_{set}$. Next, as shown at point (B), the system controller incrementally increases the value of $T_{interface}$ above the initial $T_{set}$ value (e.g. $T_{set}+X^\circ$) until the transition temperature range between vasoconstriction and vasodilation is reached. When the value of $T_{interface}$ increases above the transition temperature range as shown at point (C), vasodilation is achieved. To determine the vasoconstriction temperature, the system controller incrementally decreases the value of $T_{interface}$ until vasoconstriction occurs as shown at point (D). To account for the hysteresis phenomenon described in FIG. 9, $T_{interface}$ is then increased until vasoconstriction is again present as shown at point (E). $T_{interface}$ is then decreased to the point of T as shown at point (F). It should be recognized that when the value chosen for $T_{set}$ corresponds with vasoconstriction initially (as discussed above and shown in FIG. 11), the value of $T_{Max\ Heat\ Transfer}$ will be greater than the arbitrary value chosen for $T_{set}$. Thus, in summary, the exemplary method serves to manipulate the body portion temperature of a mammal by inducing vasodilation through raising the value of $T_{interface}$ to some point above $T_{Max\ Heat\ Transfer}$, lowering the $T_{interface}$ to some point below the vasoconstriction temperature, and again raising $T_{interface}$ to some point above $T_{Max\ Heat\ Transfer}$ before lowering $T_{interface}$ to the point of $T_{Max\ Heat\ Transfer}$.

Utility

As demonstrated above, the exemplary methods and systems provide for extracting thermal energy or heat from the core body of a mammal. As such, the subject methods are suitable for use in a variety of different applications, where representative applications include the treatment of normal and abnormal physiological conditions, e.g., disease, where core body heat extraction is desirable. Representative applications in which the subject methods find use include the treatment of exercise or work induced hypothermia, treatment of stroke, treatment of cystic fibrosis symptoms, treatment of multiple sclerosis symptoms, and the like. By treatment is meant at least an alleviation in one or more of the symptoms associated with the condition being treated, e.g. a reduction in discomfort, amelioration or elimination of symptoms, etc.

In many examples, the subject methods are employed for enhancing the ability of a mammal to perform a physical procedure or task. As such, the subject methods are suitable for use in a variety of different applications where a variety of different types of physical procedures are performed. For illustration purposes only, the following representative applications are provided. However, it should be noted that the subject methods are suitable for use in the enhancement of the physical ability of a mammal to perform a plethora of other physical procedures not described below.

One type of physical ability that may be enhanced by practicing the subject methods is athletic ability. In other words, the methods may be used to improve the ability of a mammal to perform an athletic procedure. The nature of the improvement or enhancement may vary greatly depending on the nature of the athletic procedure being practiced by the mammal. Representative enhancements include, but are not limited to: increases in strength, e.g., as measured by ability to lift a particular weight, etc.; increases in stamina, e.g., as measure in terms of ability to perform a task or play a sport without resting, etc.; increases in the ability of the mammal to perform repetitions of a physical task, e.g., weight lifts, pull-ups, etc; decreases in performance limiting afflictions, such as cramps; and the like.

Another type of physical ability that may be enhanced by practicing the subject methods is physical work ability. In other words, the subject methods may be used to improve the ability of a mammal to perform a particular work related physical procedure. Examples of work related physical procedures include, but are not limited to: physical building and maintenance of equipment, particularly in hot environments; building and construction, e.g., of homes and offices; civic structure building and maintenance, etc; working in a power plant or other industrial environment; performing in a military environment, particularly in hot environments or with heavy gear; performing in any environment where heavy gear is required. Enhancement may take many forms including, but not limited to: increasing the number of repetitive movements that may be performed; increasing the length of time a particular job may be performed without resting or cooling; reducing errors in a particular job; etc.

In many embodiments, the exemplary methods result in more than a reduction in recovery time to provide some other enhancement or improvement, as exemplified above, e.g., enhanced physical ability, increased workout capacity, etc. As mentioned above, the above athletic and work related physical procedures are merely representative of the procedures that may be enhanced using the subject methods.

Claims

Though the invention has been described in reference to several examples, optionally incorporating various features, the invention is not to be limited to that which is described or indicated as contemplated with respect to each embodiment or variation of the invention. It will be apparent to those skilled in the art that numerous modification and variations within the scope of the present invention are possible. Thus, the breadth of the present invention is to be limited only by the literal or equitable scope of the following claims—not the description provided herein. That being said,

We claim:

1. A method of transferring heat from a body portion of a mammal comprising the acts of:

determining a state of vasoconstriction or vasodilation in a portion of a body;

supplying heat to the portion of the body when vasoconstriction is determined;

removing heat from the portion of the body when vasodilation is determined, and applying negative pressure to the portion of the body.

2. The method of approach 1, wherein the portion of the body is an arterial vascular anastamosis containing portion of the body.

3. The method of approach 1 further including the act of preselecting the portion of the body.

4. The method of approach 1, wherein the act of determining vasoconstriction or vasodilation includes sensing a characteristic of the body associated with the state of vasoconstriction or vasodilation.

5. The method of approach 1, wherein the act of determining vasoconstriction or vasodilation includes measuring blood flow.

6. The method of approach 5, wherein the act of measuring blood flow further includes measuring a volume of the portion of the body.

7. The method of approach 5, wherein the act of measuring blood flow further includes measuring blood flow by laser Doppler.

8. The method of approach 5, wherein a state of vasoconstriction is associated with a first range of blood flow levels and vasodilation is associated with a second range of blood flow levels.

9. The method of approach 1, wherein the act of determining vasoconstriction or vasodilation further includes measuring heat transfer from the portion of the body.

10. The method of approach 1, wherein the act of determining vasoconstriction or vasodilation further includes measuring the temperature of the body.

11. The method of approach 1, wherein the act of determining vasoconstriction or vasodilation further includes measuring the core body temperature.

12. The method of approach 1, wherein the act of determining vasoconstriction or vasodilation further includes measuring tympanic temperature.

13. The method of approach 1, wherein the act of determining vasoconstriction or vasodilation further includes measuring skin temperature of a portion of the body.

14. The method of approach 1, wherein the act of determining vasoconstriction or vasodilation further includes measuring bio-impedance of a portion of the body.

15. The method of approach 1, wherein the act of determining vasoconstriction or vasodilation further includes measuring light absorption of a portion of the body.

16. The method of approach 1, wherein the act of determining vasoconstriction or vasodilation further includes providing an EKG.

17. The method of approach 1, wherein the act of determining vasoconstriction or vasodilation further includes providing an ECG.

18. A method comprising the acts of:
monitoring for both vasoconstriction and vasodilation in a portion of a body;
supplying heat to the portion of the body when vasoconstriction is determined;
removing heat from the portion of the body when vasodilation is determined; and
controlling at least one of vasoconstriction or vasodilation.

19. The method of approach 18, wherein controlling at least one of vasoconstriction or vasodilation includes the act of inducing vasodilation in a portion of the body.

20. The method of approach 18, wherein controlling at least one of vasoconstriction or vasodilation includes the act of inducing vasoconstriction in a portion of the body.

21. The method of approach 18, wherein the act of controlling at least one of vasoconstriction or vasodilation includes applying a surface treatment to the portion of the body.

22. The method of approach 18, wherein the act of controlling at least one of vasoconstriction or vasodilation includes influencing the thermoregulatory system of the mammal.

23. The method of approach 18, wherein the act of controlling at least one of vasoconstriction or vasodilation includes influencing the Pre-Optic Anterior Hypothalamus (POAH) of the mammal.

24. The method of approach 18, wherein the act of controlling at least one of vasoconstriction or vasodilation includes providing at least one preselected visual stimulus.

25. The method of approach 18, wherein the act of controlling at least one of vasoconstriction or vasodilation includes drug delivery.

26. The method of approach 18, wherein the act of controlling at least one of vasoconstriction or vasodilation includes adjusting the temperature of the portion of the body.

27. The method of approach 1, wherein the act of supplying heat further includes supplying sufficient heat to effect vasodilation.

28. A method of transferring heat from a body portion of a mammal comprising the acts of:
inducing a transition of a body portion from a state of vasodilation to vasoconstriction by removing heat from the body portion;
determining a transition temperature associated with the transition from vasodilation to vasoconstriction;
reestablishing vasodilation in the body portion; and
removing heat from the body portion with a temperature equal to or greater than the transition temperature.

29. The method claim 28, wherein if the body portion is initially in vasoconstriction, supplying heat until vasodilation occurs before inducing the transition from vasodilation to vasoconstriction.

30. The method of claim 28, wherein the temperature is within 2° C. of the transition from vasodilation to vasoconstriction.

31. The method of claim 28, wherein the temperature is within 1° C. of the transition from vasodilation to vasoconstriction.

32. The method of claim 28, wherein the temperature is lowered after reestablishing vasodilation without inducing vasoconstriction.

33. A method of transferring heat to or from a portion of a body of a mammal comprising the acts of:
determining a state of vasoconstriction or vasodilation in a portion of the body;
when vasodilation is determined, selecting transferring heat to or from the portion of the body; and
when vasoconstriction is determined, selecting at least one of supplying heat to the portion of the body and not removing heat from the portion of the body,
whereby optimal thermoregulatory status of the mammal is maintained.

34. A method for controlling the body temperature of a mammal comprising:
removing or supplying heat from a portion of the body,
while applying negative pressure to the portion of the body, and
maintaining the portion of the body above a temperature causing vasoconstriction in the portion of the body by a means for control employing a measured characteristic associated with a state of vasoconstriction or vasodilation of the portion of the body.

35. The method of approach 34, wherein the temperature of the portion of the body is maintained above 18° C. to 22° C.

36. The method of approach 34, further including the act of maintaining the temperature of the portion of the body below approximately 25° C.

37. A method of controlling body temperature of a mammal comprising:
placing at least a portion of the body in thermal communication with a conductor;

measuring a characteristic associated with a state of vasoconstriction or vasodilation in the portion of the body; and controlling heating or cooling of the conductor to maintain vasodilation in the portion of the body based upon a value that relates the characteristic to vasodilation.

38. The method of approach 37, wherein the value is determined by
supplying heat until vasodilation occurs,
removing heat until vasoconstriction occurs,
reestablishing vasodilation, and
 setting the value equal to or greater than a value corresponding to the
transition from vasodilation to vasoconstriction.

39. The method of approach 38 wherein the value is associated with a temperature of the conductor greater than or equal to a temperature where a transition of vasodialtion to vasoconstriction occurs.

40. A system for controlling body temperature of a mammal comprising:
a conductor adapted to interface with a body portion of the mammal;
a controller adapted to vary a temperature of the conductor;
a sensor element for sensing a characteristic associated with vasoconstriction or vasodilation of the body portion, wherein the controller adjusts the temperature of the conductor to maintain vasodilation in the portion of the body portion based upon a predetermined schedule that relates to the characteristic to vasodilation.

41. The system of claim 40, further including a heat exchange medium in thermal communication with at least a portion of the mammal and with at least a portion of the conductor.

42. A method comprising the acts of:
monitoring for both vasoconstriction and vasodilation in a specific portion of a body;
supplying heat to said specific portion of the body when vasoconstriction is determined; and
removing heat from said specific portion of the body when vasodilation is determined.

43. The method of approach 42, wherein the act of determining vasoconstriction or vasodilation includes sensing a characteristic of the body associated with the state of vasoconstriction or vasodilation.

44. The method of approach 43, wherein the act of determining vasoconstriction or vasodilation includes measuring blood flow.

* * * * *

UNITED STATES PATENT AND TRADEMARK OFFICE
CERTIFICATE OF CORRECTION

| | | |
|---|---|---|
| PATENT NO. | : 7,122,047 B2 | Page 1 of 1 |
| APPLICATION NO. | : 10/714488 | |
| DATED | : October 17, 2006 | |
| INVENTOR(S) | : Dennis A. Grahn | |

It is certified that error appears in the above-identified patent and that said Letters Patent is hereby corrected as shown below:

In the Specification:

- In Column 1, prior to the Background beginning on line 11, insert the following header and paragraph:

--FEDERALLY SPONSORED RESEARCH AND DEVELOPMENT

This invention was made with Government support under contract NBCH1030020 awarded by The Department of the Interior, contract M67854-00-C-2144a, awarded by the Marine Corps Systems Command, and contracts DAMD17-03-2-0029, W911NF-05-1-0548, W911NF-07-1-0098 awarded by The Department of the Army. The Government has certain rights in this invention.--

Signed and Sealed this

Eighteenth Day of October, 2011

David J. Kappos
*Director of the United States Patent and Trademark Office*